US 12,036,052 B2

(12) United States Patent
Schmotz et al.

(10) Patent No.: US 12,036,052 B2
(45) Date of Patent: Jul. 16, 2024

(54) PATIENT SUPPORT APPARATUS WITH RADIATION SENSOR

(71) Applicant: Baxter Medical Systems GmbH + Co. KG, Saalfeld (DE)

(72) Inventors: Christoph Schmotz, Munich (DE); Mattes Papendieck, Neuenhagen bei Berlin (DE); Dieter Ceglarz, Munich (DE)

(73) Assignee: Baxter Medical Systems GmbH + Co. KG, Saalfeld (DE)

( * ) Notice: Subject to any disclaimer, the term of this patent is extended or adjusted under 35 U.S.C. 154(b) by 0 days.

(21) Appl. No.: 18/139,147

(22) Filed: Apr. 25, 2023

(65) Prior Publication Data

US 2023/0255574 A1 Aug. 17, 2023

Related U.S. Application Data

(62) Division of application No. 17/071,278, filed on Oct. 15, 2020, now Pat. No. 11,666,289.

(60) Provisional application No. 62/923,069, filed on Oct. 18, 2019.

(51) Int. Cl.
  *A61B 6/04* (2006.01)
  *A61B 6/00* (2006.01)
  *A61B 6/46* (2024.01)

(52) U.S. Cl.
  CPC .......... *A61B 6/0407* (2013.01); *A61B 6/0487* (2020.08); *A61B 6/0492* (2013.01); *A61B 6/461* (2013.01); *A61B 6/542* (2013.01)

(58) Field of Classification Search
  CPC ....... A61B 6/032; A61B 6/4441; A61B 6/037; A61B 6/548; A61B 6/4405; A61B 6/04; A61B 6/4435; A61B 6/4452; A61B 8/13; A61B 8/40; A61B 5/00; A61B 5/0013; A61B 5/0026
  See application file for complete search history.

(56) References Cited

U.S. PATENT DOCUMENTS

| 8,788,292 | B2 | 7/2014 | Bourdeaux et al. |
| 9,913,623 | B2 | 3/2018 | Ohishi |
| 2007/0201617 | A1 | 8/2007 | Nakayama et al. |
| 2008/0080673 | A1 | 4/2008 | Yamakita |
| 2009/0010391 | A1 | 1/2009 | Kito et al. |
| 2010/0208871 | A1 | 8/2010 | Tanabe et al. |

(Continued)

FOREIGN PATENT DOCUMENTS

| CN | 106456087 A | * | 2/2017 | ............... A61B 6/04 |
| EP | 1772101 A | | 11/2007 | |

(Continued)

*Primary Examiner* — Don K Wong
(74) *Attorney, Agent, or Firm* — Price Heneveld LLP

(57) ABSTRACT

A radiation monitoring system includes a patient support apparatus. A radiation sensor assembly is operably coupled to the patient support apparatus. The radiation sensor assembly includes a radiation sensor and a first controller. The radiation sensor senses radiation data corresponding to a radiation dose received by a patient. A management system includes a second controller that stores a patient profile database. The second controller is communicatively coupled with the first controller. The first controller communicates the radiation data to the second controller for storage in the patient profile database to monitor the radiation dose received by the patient.

20 Claims, 8 Drawing Sheets

(56) References Cited

U.S. PATENT DOCUMENTS

| | | |
|---|---|---|
| 2011/0296613 A1 | 12/2011 | Farmbauer et al. |
| 2015/0224343 A1 | 8/2015 | Couture et al. |
| 2018/0133508 A1 | 5/2018 | Pearce et al. |
| 2018/0168534 A1 | 6/2018 | Desponds |

FOREIGN PATENT DOCUMENTS

| | | |
|---|---|---|
| EP | 2349475 B1 | 1/2016 |
| EP | 3367900 B1 | 7/2019 |
| JP | 4714110 B2 | 6/2011 |
| JP | 2011136054 A | 7/2011 |
| JP | 2017189392 A | 10/2017 |
| WO | 2010025114 A1 | 3/2010 |
| WO | 2017074792 A1 | 5/2017 |

* cited by examiner

PATIENT SUPPORT APPARATUS WITH RADIATION SENSOR

CROSS-REFERENCE TO RELATED APPLICATIONS

This application is a divisional of U.S. patent application Ser. No. 17/071,278, filed on Oct. 15, 2020, now U.S. Pat. No. 11,666,289, entitled "PATIENT SUPPORT APPARATUS WITH RADIATION SENSOR," which claims priority to and the benefit under 35 U.S.C. § 119(e) of U.S. Provisional Application No. 62/923,069, filed on Oct. 18, 2019, entitled "PATIENT SUPPORT APPARATUS WITH RADIATION SENSOR," each disclosure of which is hereby incorporated herein by reference in its entirety.

FIELD OF THE DISCLOSURE

The present disclosure generally relates to a patient support apparatus that includes a radiation sensor.

SUMMARY OF THE DISCLOSURE

According to one aspect of the present disclosure, a radiation monitoring system includes a patient support apparatus. A radiation sensor assembly is operably coupled to the patient support apparatus. The radiation sensor assembly includes a radiation sensor and a first controller. The radiation sensor senses radiation data corresponding to a radiation dose received by a patient. A management system includes a second controller that stores a patient profile database. The second controller is communicatively coupled with the first controller. The first controller communicates the radiation data to the second controller for storage in the patient profile database to monitor the radiation dose received by the patient.

According to another aspect of the present disclosure, a patient support apparatus includes a support member coupled to a base. A radiation sensor assembly is operably coupled to the support member. The radiation sensor assembly includes at least one radiation sensor for sensing radiation data to monitor a radiation dose received by a patient. A positioning assembly is operably coupled to the radiation sensor assembly and the support member. The radiation sensor assembly translates between a first end of the support member and a second end of the support member via the positioning assembly. The radiation sensor assembly remains operably coupled with the support member as the radiation sensor assembly is translated.

According to yet another aspect of the present disclosure, a method of monitoring a radiation dose includes: aligning a radiation sensor assembly with a selected area to receive radiation. Radiation is emitted toward a patient support apparatus. Radiation data corresponding to a radiation dose received by a patient is sensed via a radiation sensor assembly. The radiation data is communicated from a first controller of the radiation sensor assembly operably coupled with the patient support apparatus to a second controller of a management system. The radiation data is stored within a selected profile within the management system.

These and other features, advantages, and objects of the present disclosure will be further understood and appreciated by those skilled in the art by reference to the following specification, claims, and appended drawings.

DETAILED DESCRIPTION

Figure 1:
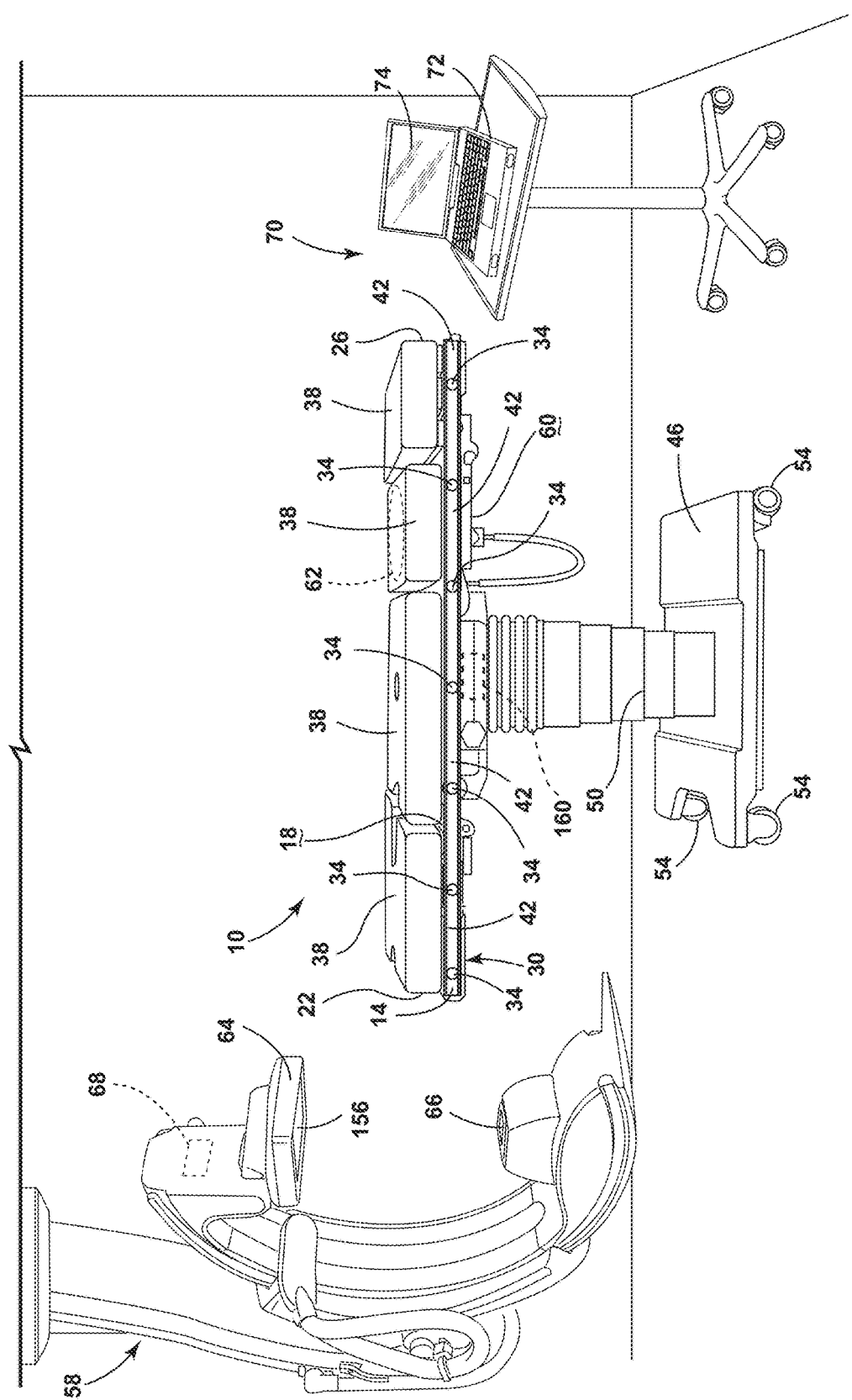
FIG. 1 is a side perspective view of surgical suite accessories within a surgical suite, according to the present disclosure.

The present illustrated embodiments reside primarily in combinations of method steps and apparatus components related to a patient support apparatus with a radiation sensor. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-11 reference numeral 10 generally designates a patient support apparatus that includes a support member 14 that has a patient support surface 18 and has first and second ends 22, 26. A radiation sensor assembly 30 includes a radiation sensor 34. The radiation sensor assembly 30 is operably coupled with the support member 14 and configured to translate between the first and second ends 22, 26.

Referring to FIG. 1, the patient support apparatus 10 is illustrated as a surgical table. The patient support apparatus 10 includes the patient support surface 18 for supporting a patient thereon. In various examples, pads 38 are disposed on the patient support surface 18. As illustrated in FIG. 1, the patient support apparatus 10 includes multiple pads 38 arranged on the patient support surface 18 between the first and second ends 22, 26. The pads 38 may be spaced apart from one another and define spaces therebetween, or alternatively, may be directly coupled to one another. Alternatively, the patient support apparatus 10 may include a single pad 38 covering at least a portion of the patient support surface 18. The pads 38 may also be selectively coupled with the patient support surface 18. In such examples, the pads 38 may be coupled with the patient support surface 18 by snap features, hooks, Velcro®, or other similar fasteners.

According to various aspects, the support member 14 includes multiple segments 42. The segments 42 are generally independently movable relative to one another. In this way, a single segment 42 may be rotated to an incline, a decline, or otherwise moved relative to the adjacent segments 42. The independently movable segments 42 may be advantageous for aligning the patient on the patient support surface 18 for one or more surgical procedures, imaging procedures, or other similar procedures. It is also contemplated that the support member 14 is a single segment 42.

The patient support apparatus 10 includes a base 46 and a pedestal 50 that extends between the base 46 and the support member 14. As illustrated in FIG. 1, the pedestal 50 is centrally located relative to the support member 14. While the patient support apparatus 10 is illustrated with a single central pedestal 50, it is contemplated that more than one pedestal 50 may extend between the support member 14 and the base 46. It is also contemplated that the pedestal 50 may be coupled to the support member 14 at any practicable position between the first and second ends 22, 26. In various examples, the base 46 includes rollers 54. In such examples, the patient support apparatus 10 may be transportable around a surgical suite or otherwise within a hospital or other medical facility.

Referring still to FIG. 1, the patient support apparatus 10 may be operably coupled with a radiation unit 58. The radiation unit 58 is generally movable relative to the patient support apparatus 10. In this way, the radiation unit 58 may align with a selected part of the patient support apparatus 10 to perform one or more imaging procedures. In a non-limiting example, the radiation unit 58 may be an X-ray machine configured to emit electromagnetic waves (e.g., radiation) having a wavelength in a range of from about 0.01 nm to about 10 nm.

In the illustrated example of FIG. 1, the radiation unit 58 is a C-arm X-ray machine that includes an emitter 64 and a detector 66. The emitter 64 is disposed above the patient proximate to the patient support surface 18, and the detector 66 is disposed below the patient proximate to a lower surface 60 of the support member 14. The electromagnetic waves (e.g., X-rays) may be directed at a selected focus area 62 on the patient support apparatus 10, and consequently the patient, by the emitter 64. The electromagnetic waves may at least partially pass through the support member 14 and the patient disposed thereon to be received by the detector 66. The radiation unit 58 generally sends detected data from the detector 66 to a control unit 68 of the radiation unit 58, which analyzes the detected data to produce an image representative of shadows formed by objects inside the body (e.g., to produce the X-ray image). A surgeon, or other medical personnel, can adjust and align the radiation unit 58 relative to the patient support apparatus 10 to obtain imaging of the patient during the one or more surgical procedures. It is contemplated that the detector 66 may be part of the radiation unit 58, or alternatively, may be part of the radiation sensor assembly 30. It is contemplated that other types of imaging machines may be utilized without departing from the teachings herein. Further, it is contemplated that the radiation unit 58 may also be utilized for various treatments for the patient.

Multiple surgical suite accessories 70 are generally positioned in the surgical suite during the surgical procedures. The surgical suite accessories 70 include, for example, the patient support apparatus 10, the radiation unit 58, a user interface assembly 72, other medical equipment, storage, etc. The user interface assembly 72 receives inputs from the medical personnel regarding the patient, the surgical procedures, the imaging procedures, or other aspects of the surgical suite environment. The user interface assembly 72 may include a display screen 74 to provide visual outputs to the medical personnel within the surgical suite. For example, the imaging obtained by the radiation unit 58 may be viewed on the display screen 74 during or after the surgical procedures.

Referring still to FIG. 1, the patient support apparatus 10 may be operably coupled with the radiation sensor assembly 30. The radiation sensor assembly 30 includes at least one radiation sensor 34, which is generally coupled to the support member 14. The radiation sensor 34 may be operably coupled with the patient support surface 18, or alternatively, another practicable surface of the support member 14 (e.g., a side surface, the lower surface 60, etc.). The radiation sensor 34 may be integrally formed with the support member 14, or alternatively, removably coupled with the support member 14. The radiation sensor assembly 30 may also be disposed in an interior of the support member 14.

Figure 2:
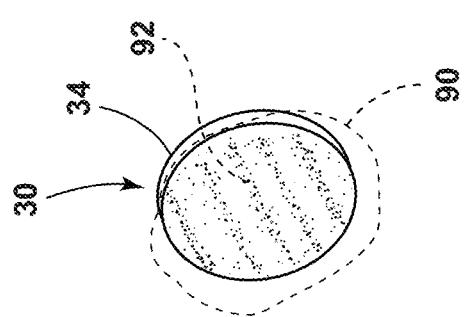
FIG. 2 is a rear perspective view of a radiation sensor with an adhesive portion and a cover film, according to the present disclosure.

Referring still to FIG. 1, as well as FIG. 2, the radiation sensor assembly 30 may be substantially stationary on the patient support apparatus 10. For example, the radiation sensor assembly 30 may be adhered to the patient support apparatus 10. Additionally or alternatively, the radiation sensor assembly 30 may be coupled to the support member 14 via hook and loop fasteners, snap features, buttons, clips, other fasteners or coupling members, or a combination thereof. In such examples, a cover film 90 may be removed from the radiation sensor assembly 30 that exposes an adhesive portion 92 on the radiation sensor assembly 30.

The adhesive portion 92 couples the radiation sensor assembly 30 with the support member 14. The radiation sensor assembly 30 may be applied to a selected location on the patient support apparatus 10. The radiation sensor assembly 30 with the adhesive portion 92 may be disposable or single-use, or alternatively, the adhesive portion 92 may be configured for multiple uses in multiple locations on the patient support apparatus 10. In another non-limiting example, the adhesive portion 92 of the radiation sensor assembly 30 may be replaceable, such that the radiation sensor assembly 30 may be reused. In such examples, the adhesive portion 92 is configured as an adhesive pad that is adhered to the radiation sensor assembly 30 on one side and adhered to the support member 14 on the opposing side. After completion of the surgical or imaging procedures, the radiation sensor assembly 30 may be removed from the patient support apparatus 10, and the adhesive pad may be removed from the radiation sensor assembly 30 to be disposed. A new adhesive pad may then be used for subsequent uses of the radiation sensor assembly 30.

Figure 3:
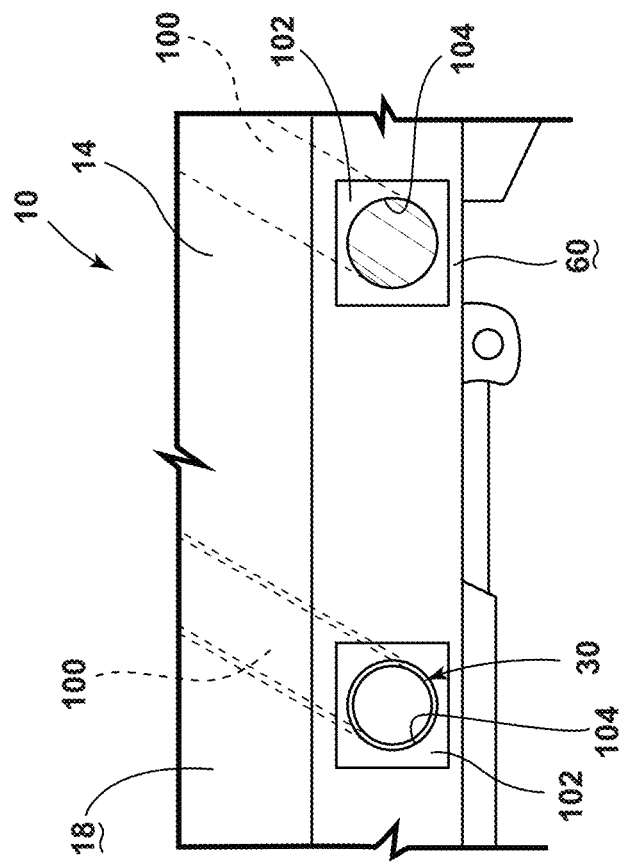
FIG. 3 is a partial side perspective view of a patient support apparatus with a radiation sensor assembly disposed within a cavity defined in the patient support apparatus, according to the present disclosure.

Referring to FIG. 3, the radiation sensor assembly 30 may be manually adjusted to different predetermined locations on the support member 14. The patient support apparatus 10 may define multiple cavities 100 for receiving the radiation sensor assembly 30. The cavities 100 may be selectively enclosed by an at least partially transparent window 102, such that the medical personnel can see whether the radiation sensor assembly 30 is positioned within a selected cavity 100.

The medical personnel may adjust the window 102 to access the cavity 100 and then cover the cavity 100 when the radiation sensor assembly 30 is disposed within the cavity 100. The window 102 may slide, pivot, or otherwise adjust to selectively allow access and enclose the selected cavity 100. Alternatively, a substantially opaque panel may enclose one of the cavities 100 to obscure the radiation sensor assembly 30 from view. The windows 102 and panels may be interchangeable, such that the cavity 100 with the radiation sensor assembly 30 may be enclosed with the window 102 and the empty cavities 100 may be enclosed with panels. This arrangement may be advantageous for quickly indicating to the medical personnel the location of the radiation sensor assembly 30. The medical personnel may manually move the radiation sensor assembly 30 between the cavities 100. Multiple cavities 100 may include the radiation sensor assembly 30 simultaneously. For example, the radiation sensor assembly 30 may include multiple radiation sensors 34 that may be disposed in separate cavities 100. The cavities 100 may be accessed from apertures 104 defined on the patient support surface 18, the lower surface 60, or a side surface of the support member 14.

Figure 4:
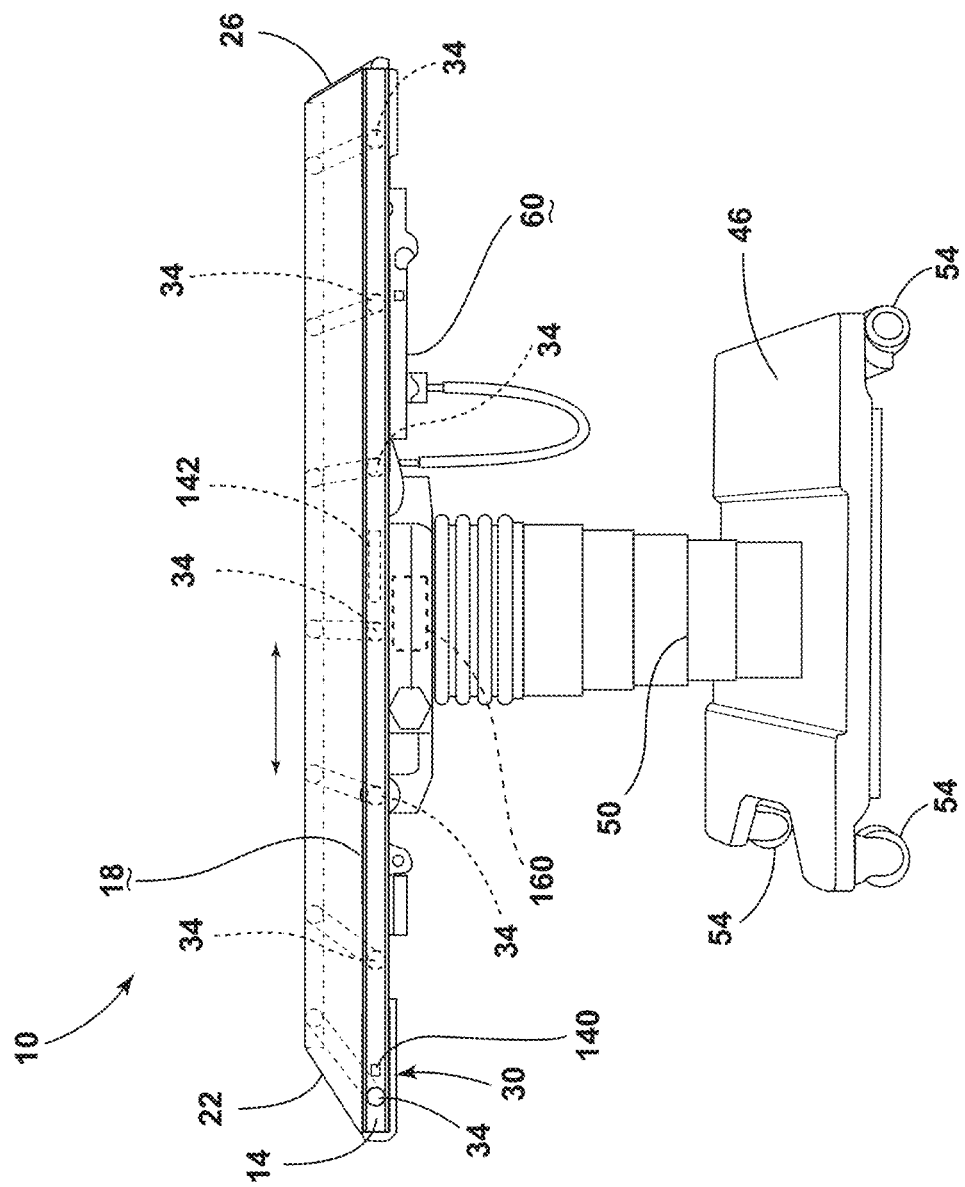
FIG. 4 is a side perspective view of a patient support apparatus with a radiation sensor assembly that translates between first and second ends of the patient support apparatus, according to the present disclosure.

Referring to FIG. 4, at least part of the radiation sensor assembly 30 may be configured to translate between the first and second ends 22, 26 of the support member 14. The adjustable radiation sensor assembly 30 may be advantageous for aligning the radiation sensor assembly 30 with the focus area 62 of the radiation unit 58 between the emitter 64 and the detector 66, such that the radiation sensor 34 may sense radiation data that corresponds to the radiation emitted from the radiation unit 58 (FIG. 1). It is contemplated that the entire radiation sensor assembly 30 may adjust to different positions, or alternatively, the radiation sensor 34 may be adjusted without the remainder of the radiation sensor assembly 30.

Figure 5:
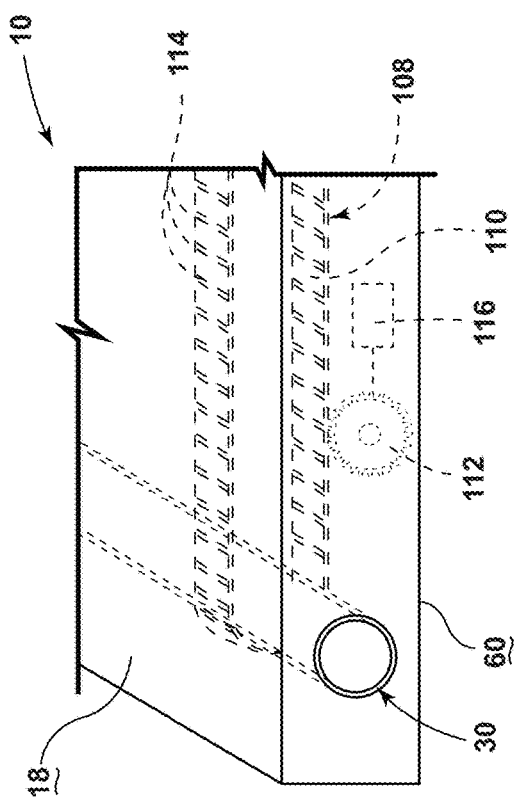
FIG. 5 is a partial side perspective view of a patient support apparatus with a radiation sensor assembly adjustable via a belt and a gear assembly, according to the present disclosure.

Referring to FIG. 5, the radiation sensor assembly 30 may be mechanically adjusted between the first and second ends 22, 26 of the support member 14 by a positioning assembly 108. It is contemplated that the positioning assembly 108 may be motorized, or may be manually operated. For example, the positioning assembly 108 may include a belt 110 that engages a gear assembly 112. The radiation sensor assembly 30 may be coupled to a belt 110 that defines teeth 114 arranged along a length of the belt 110. The teeth 114 of the belt 110 engage the gear assembly 112 to move the radiation sensor assembly 30 between the first and second ends 22, 26.

A motor 116 may be operably coupled with the gear assembly 112. The motor 116 may be activated through the user interface assembly 72 (FIG. 1). The medical personnel may control the motor 116 until the radiation sensor assembly 30 is in the selected position. Alternatively, the medical personnel may input a selected location, which may be any location or a predefined location, and the radiation sensor assembly 30 may be adjusted to the selected location. The belt 110 and the gear assembly 112 may be disposed within the interior of the support member 14. This configuration may be advantageous for minimizing interference between the belt 110 and the medical personnel.

Figure 6:
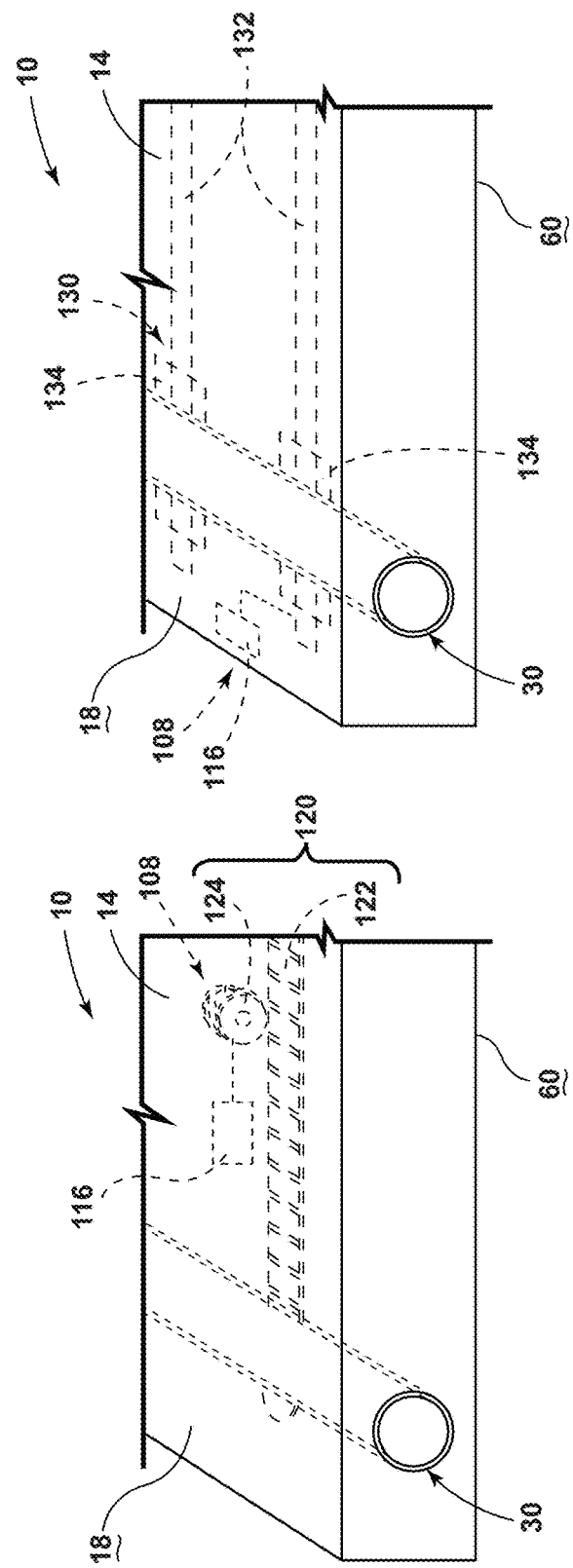
FIG. 6 is a partial side perspective view of a patient support apparatus with a radiation sensor assembly adjustable via a worm gear assembly, according to the present disclosure.

Referring to FIG. 6, the positioning assembly 108 may be configured as a worm gear assembly 120. The radiation sensor assembly 30 may be coupled to a first worm gear 122 that engages a second worm gear 124 operably coupled with the motor 116. The first worm gear 122 engages the second worm gear 124 to adjust the radiation sensor assembly 30 between the first and second ends 22, 26 of the support member 14. As previously described, the motor 116 may be activated through the user interface assembly 72 and may be operated to adjust the radiation sensor assembly 30 to the selected position.

Figure 7:
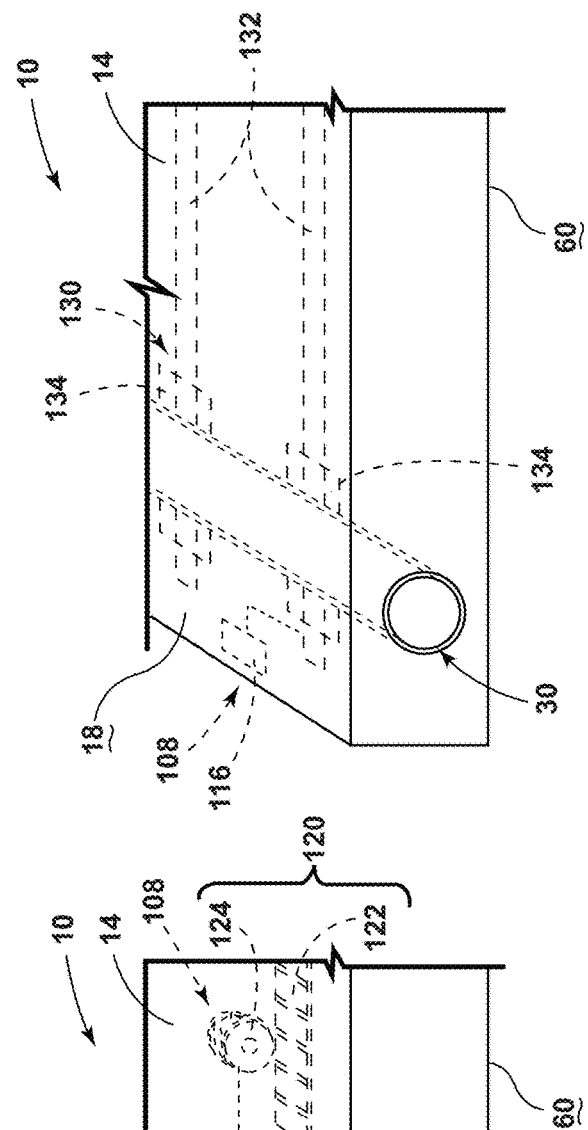
FIG. 7 is a partial side perspective view of a patient support apparatus with a radiation sensor assembly adjustable via a rail assembly, according to the present disclosure.

Referring to FIG. 7, in another non-limiting example, the positioning assembly 108 may be a rail assembly 130. In such examples, at least one rail 132 may be coupled to the support member 14 and the radiation sensor assembly 30 may be coupled to a rail slide 134. The rail slide 134 with the radiation sensor assembly 30 may slidably engage the rail 132 to adjust the radiation sensor assembly 30 between the first and second ends 22, 26. The rail slide 134 may be operably coupled with the motor 116 to adjust the rail slide 134 along the rail 132. As previously explained, the motor 116 may be activated and controlled through the user interface assembly 72.

The support member 14 may include one or more positioning assemblies 108. For example, the rail assembly 130 may include two rails 132 extending along a longitudinal extent of the support member 14. In such configurations, the radiation sensor assembly 30 may include two slides 134. Alternatively, the radiation sensor assembly 30 may include more than one radiation sensor 34, with each radiation sensor 34 coupled to a separate rail slide 134 for engaging one of the rails 132. The separate radiation sensors 34 may be adjusted simultaneously or independently. It is contemplated that each positioning assembly 108 described herein may also be manually adjusted through a handle or similar device without departing from the teachings herein.

Referring to FIGS. 1-7, the radiation sensor assembly 30 may be positioned at any practicable location on the support member 14. Additionally or alternatively, the radiation sensor assembly 30 may be adjusted between predefined regions of the support member 14 or to any selected locations. When the radiation sensor assembly 30 is disposed in a certain region or arrives at a selected location, an indicator 140 may notify the medical personnel that the radiation sensor assembly 30 is positioned within the specified region or at the selected location. The indicator 140 may be an icon, an illuminated feature, a button position, or another visual, tactile, or audio indicator. The indicator 140 may be disposed on the patient support apparatus 10, the radiation sensor assembly 30, the user interface assembly 72, or a combination thereof. For example, when the radiation sensor assembly 30 is in a certain region or a certain cavity 100, a light on the patient support apparatus 10 proximate to the region or cavity 100 may illuminate. In another example, a graphical representation of the position of the radiation sensor assembly 30 may be displayed on the user interface assembly 72. It is contemplated that the radiation sensor assembly 30 or the patient support apparatus 10 may include a position sensor 142 or a proximity sensor for determining the location of the radiation sensor assembly 30 relative to the patient support apparatus 10. The position sensor 142 may be included in the patient support apparatus 10, the radiation sensor assembly 30, or a combination thereof.

Figure 8:
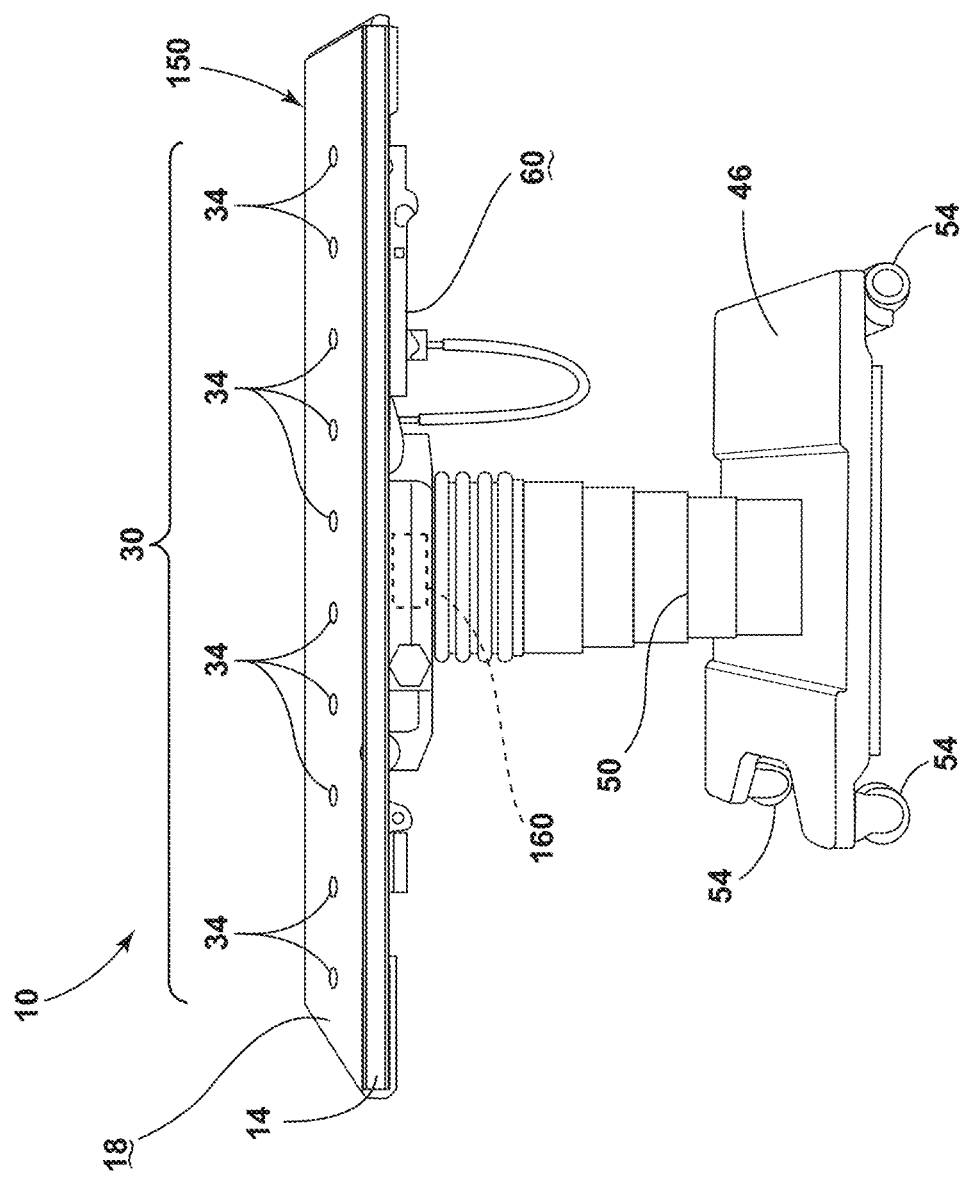
FIG. 8 is a side perspective view of a patient support apparatus with an array of radiation sensors, according to the present disclosure.

Referring to FIG. 8, the radiation sensor assembly 30 may include multiple radiation sensors 34 arranged in an array 150. The radiation sensors 34 of the array 150 are generally spaced apart along the support member 14. In the illustrated configuration, the radiation sensors 34 are disposed along a central longitudinal axis. Alternatively, the radiation sensors 34 may be disposed on opposing sides of the support member 14 relative to the central longitudinal axis or in any other practicable arrangement. The radiation sensors 34 may be mechanically or manually adjustable to any practicable positions on the support member 14 as previously described herein.

The array 150 may correspond with the predefined regions of the patient support apparatus 10. One or a grouping of radiation sensors 34 of the array 150 may be disposed in each predefined region. The positions of the radiation sensors 34 may be adjusted within their respective predefined region. The predefined regions may correspond with the multiple segments 42 of the support member 14. The radiation sensors 34 of the array 150 may be independently or selectively activated based on the location of the radiation unit 58 or an input by the medical personnel through the user interface assembly 72. It is also contemplated that multiple radiation sensor assemblies 30 may be arranged in the array 150.

Referring to FIGS. 1-8, the radiation sensors 34 sense the radiation data that corresponds to the radiation emitted from the radiation unit 58. It is contemplated that the radiation sensors 34 may each detect radiation in discrete areas along the support member 14 or may individually or collectively detect radiation over the entire support member 14. Accordingly, the radiation sensor 34 may be configured as a single sensor, the array 150 of radiation sensors 34, a sensing layer extending across the support member 14, etc. The radiation sensors 34 sense the radiation data in the form of electromagnetic waves that have a wavelength in a range of from about 0.01 nm to about 10 nm (e.g., X-rays). The radiation data sensed by the radiation sensors 34 is generally indicative of or corresponds to a radiation dose received by the patient on the patient support apparatus 10. The radiation sensors 34 may be utilized to monitor the radiation dose received by the patient during the imaging procedures conducted during the surgical or other procedures.

According to various aspects, the radiation unit 58 may emit X-rays with energies in a range of from about 100 eV to about 100 keV. X-rays may be categorized as hard X-rays or soft X-rays based on their energies. Typically, hard X-rays have energies above a range of from about 5 eV to about 10 keV, which corresponds with a wavelength in a range from about 0.2 nm to about 0.1 nm. Hard X-rays are typically more helpful for medical radiography (e.g., the imaging procedures) as the hard X-rays pass through the human body to the detector 66. Further, as the hard XX-rays pass through the human body, the hard X-rays are generally used to create the shadow effect that creates the X-ray image in medical radiography.

Soft X-rays typically exhibit energies in a range of from about 100 eV to about 5 keV, which corresponds with a wavelength in a range from about 10 nm to about 0.1 nm. Soft X-rays may be absorbed by the body or air within the surgical suite, which may increase the radiation dose received by the patient. As such, soft X-rays may be limited when in the surgical suite by a filter 156 included in the radiation unit 58. The filter 156 may be placed over the emitter 64 to absorb the low-energy part of the spectrum (e.g., the soft X-rays). The filter 156 may be a thin metal sheet, which is often constructed of aluminum. The process of filtering the radiation is often referred to as hardening the beam, as the filter 156 shifts the center of the emitted spectrum toward higher energy X-rays (e.g., hard X-rays). As such, the radiation sensor 34 may sense hard X-rays emitted from the radiation unit 58 more than soft X-rays and may be calibrated accordingly.

Figure 9:
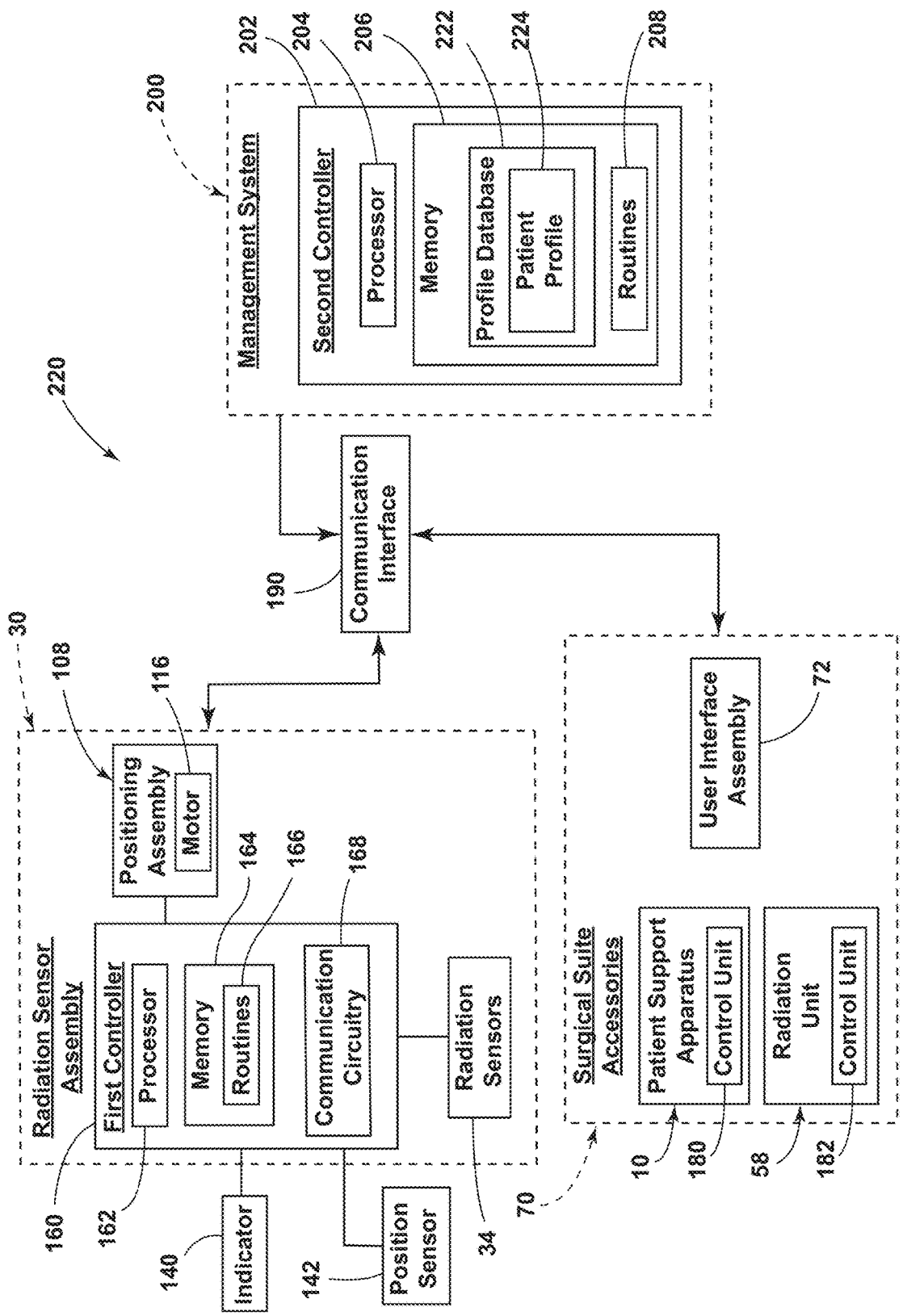
FIG. 9 is a block diagram of a radiation monitoring system, according to the present disclosure.

Referring to FIG. 9, the radiation sensor assembly 30 includes a first controller 160, which includes a processor 162, a memory 164, and other control circuitry. Instructions or routines 166 are stored within the memory 164 and executable by the processor 162. For example, the first controller 160 generally includes at least one routine 166 for activating or deactivating the motor 116. The first controller 160 is configured for gathering input, processing the input, and generating an output response to the input.

The first controller 160 may also include at least one routine 166 to analyze the radiation data sensed by the radiation sensors 34. For example, the processor 162 may analyze whether the sensed radiation data includes hard X-rays, soft X-rays, or a combination thereof. The first controller 160 may determine the amount of each of the hard and soft X-rays sensed by the radiation sensors 34. In examples with multiple radiation sensors 34, the first controller 160 is communicatively coupled with each radiation sensor 34 to receive the respective sensed radiation data. The first controller 160 may determine which radiation sensor 34 sensed the received radiation data. The first controller 160 may also correlate the respective radiation sensor 34 with a location on the patient support apparatus 10, which may be determined by the position sensor 142 or may be a stored location within the memory 164. The first controller 160 of the radiation sensor assembly 30 also includes communication circuitry 168 for receiving inputs and transmitting outputs. The communication circuitry 168 may be any practicable circuitry for exchanging data.

The radiation sensor assembly 30 may be in communication with a control unit 180, which may be integrated into the patient support apparatus 10, or alternatively, may be disposed elsewhere in the surgical suite. The first controller 160 may communicate the sensed radiation data to the control unit 180. Additionally or alternatively, the first controller 160 may activate or adjust the radiation sensors 34 in response to information received from the control unit 180 (e.g., positioning, orientation, etc.).

The first controller 160 may communicate with the control unit 68 of the radiation unit 58. The first controller 160 may activate or adjust the radiation sensors 34 in response to information received from the control unit 68. The information may relate to the position or status of the emitter 64 or the detector 66 or a specific setting for the electromagnetic waves to be emitted. In response to receiving the information from the control unit 68, the radiation sensor assembly 30 may scale measurements for the sensed radiation data based on the expected wavelength range of the radiation emitted from the radiation unit 58 (e.g., hard X-rays, soft X-rays, etc.). This adjustment may be advantageous for increasing accuracy or efficiency of the radiation sensors 34, which may increase the accuracy of the sensed radiation dose.

Referring still to FIG. 9, the radiation sensor assembly 30 is in communication with the user interface assembly 72. The radiation sensors 34 may be selectively activated by an input received by the user interface assembly 72. The medical personnel may input a selected radiation sensor 34 into the user interface assembly 72 and a selected position or location in the support member 14. The user interface assembly 72 may send a signal indicating the selected radiation sensor 34 to be activated to the first controller 160. Accordingly, different regions or zones of radiation sensors 34 may be selectively activated based on the focus area 62 of the radiation unit 58. The position of the focus area 62 may be selected or input by the medical personnel via the user interface assembly 72 or otherwise communicated to the radiation sensor assembly 30. The radiation sensor assembly 30 may communicate with each of the control unit 180 of the patient support apparatus 10, the control unit 68 of the radiation unit 58, and the user interface assembly 72 via a communication interface 190.

The first controller 160 may also communicate with a management system 200 via the communication interface 190. The management system 200 includes a second controller 202 generally includes a processor 204, a memory 206, and other control circuitry. Instructions or routines 208 are stored within the memory 206 and executable by the processor 204. The second controller 202 also includes communication circuitry 210 configured for bidirectional communication.

In a non-limiting example, the communication interface 190 may include a network. The network may be one or more various wired or wireless communication mechanisms, including any combination of wired (e.g., cable and fiber) and/or wireless communications and any network topology or topologies. Exemplary communication networks include wireless communication networks, such as, for example, a Bluetooth® transceiver, a ZigBee® transceiver, a WiFi transceiver, an Infrared Data Association (IrDA) transceiver, a radio-frequency identification (RFID) transceiver, etc. The first and second controllers 160, 202 may include circuitry configured for bidirectional wireless communication. Additional exemplary networks include local area networks (LAN) and/or wide area networks (WAN), including the Internet or other data communication services. It is contemplated that the first and second controllers 160, 202 may communicate by any suitable technology for exchanging data. Each of the first and second controller 160, 202 may include transceivers, or separate transmitters and receivers. In examples using the Bluetooth® transceiver, the first and second controller 160, 202 may be linked or synchronized (e.g., synced).

Referring still to FIG. 9, the management system 200 may include remote devices or servers that store information. The management system 200 generally stores Electronic Medical Records and Electronic Health Records of patients associated with the medical facility. The management system 200 may also store information regarding medical personnel, equipment, various workflow or treatment programs or software, etc.

The radiation sensor assembly 30 and the management system 200 may be included in a radiation monitoring system 220 of the hospital or medical facility. The management system 200 generally stores a patient profile database 222 within the memory 206. The patient profile database 222 stores the Electronic Medical Records, the Electronic Health Records, and other patient information within patient profiles 224.

Referring still to FIG. 9, the radiation monitoring system 220 operates to sense and store the radiation dose for a patient during imaging procedures, treatments, etc. The radiation dose received by the patient during the various procedures may be automatically stored in the patient profile 224. The radiation dose may also be displayed to the medical personnel in the surgical suite via the user interface assembly 72. The communication interface 190 provides communication between various features of the radiation monitoring system 220, including between the radiation sensor assembly 30, the patient support apparatus 10, the radiation unit 58, and the user interface assembly 72, as well as between the radiation sensor assembly 30 and the management system 200.

Figure 10:
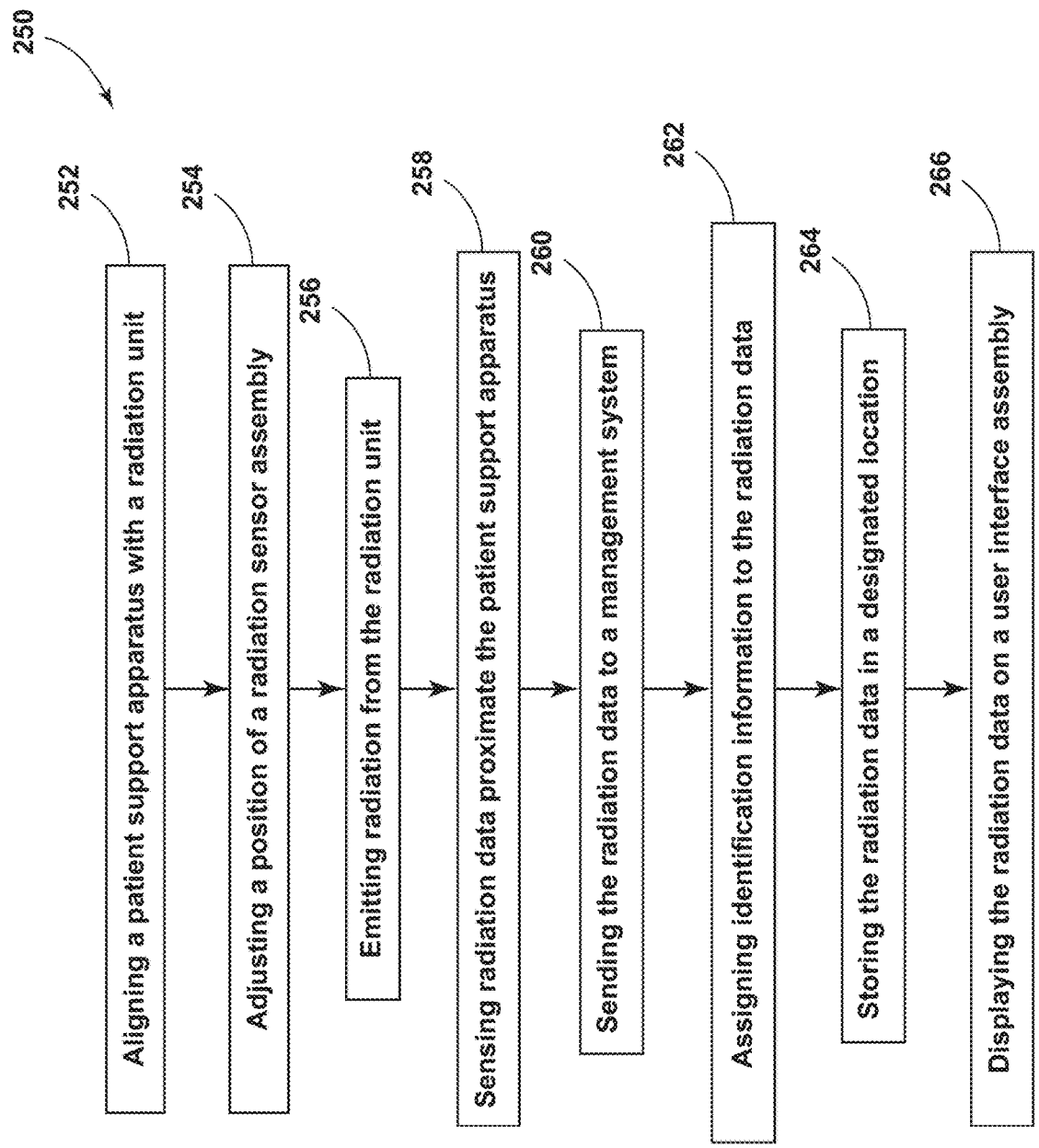
FIG. 10 is a flow diagram of a method of monitoring a radiation dose, according to the present disclosure.

Referring to FIG. 10, as well as FIGS. 1-9, a method 250 of monitoring the radiation dose includes step 252 of aligning the patient support apparatus 10 with the radiation unit 58. The radiation unit 58 may be disposed over the patient support apparatus 10, such that the focus area 62 is aimed at a selected portion of the patient on the support member 14. The focus area 62 may be limited to the selected area to reduce exposure to radiation to other areas of the patient. The radiation unit 58 may include a lens or similar device for limiting the focus area 62 or directing the emitted radiation.

In step 254, the radiation sensor assembly 30 may be adjusted to a selected position between the emitter 64 and the detector 66. This adjustment may be accomplished manually or automatically via the positioning assembly 108. Step 254 may also include aligning the filter 156 on the emitter 64 for reducing the soft X-rays that are emitted toward the patient.

Step 256 includes emitting the radiation from the radiation unit 58. The medical personnel may activate the radiation unit 58 via the user interface assembly 72, which communicates with the control unit 68 of the radiation unit 58. The radiation unit 58 emits radiation toward the patient support apparatus 10 within the focus area 62. The medical personnel may deactivate the radiation unit 58 by a subsequent input to the user interface assembly 72. Additionally or alternatively, the radiation unit 58 may automatically deactivate after a predetermined time, or after emitting a predetermined radiation dose. In examples where the radiation unit 58 deactivates after emitting the predetermined radiation dose, the radiation dose may be sensed by the radiation sensors 34 and compared to a selected radiation dose by the first controller 160.

In step 258, the radiation data is sensed by the radiation sensor assembly 30. The radiation data sensed may be radiation proximate to the patient support surface 18 of the patient support apparatus 10, and consequently, may be the radiation dose received by the patient. In step 258, the radiation sensor assembly 30 analyzes the radiation dose of hard X-rays and/or soft X-rays sensed by the radiation sensors 34. The radiation sensor assembly 30 may also analyze the duration of exposure to the radiation.

In step 260, the first controller 160 of the radiation sensor assembly 30 communicates the radiation data to the second controller 202 via the communication interface 190. Generally, the first controller 160 is coupled with the patient support apparatus 10 and the second controller 202 is separate from the patient support apparatus 10. The sensed data, the analyzed data, or a combination thereof may be communicated to the second controller 202 of the management system 200. Step 260 may also include communicating the sensed data, the analyzed data, or a combination thereof to the user interface assembly 72. The communication to the management system 200 may be substantially concurrent with the communication to the user interface assembly 72.

Step 262 may include assigning identification information to the radiation data received in the management system 200. The identification information may include a date, a time, a location, or a combination thereof in which the radiation data was sensed. Step 262 may also include confirming whether the radiation data received in the management system 200 was received with a patient name or other patient identification associated with the radiation data.

In step 264, the second controller 202 may store the radiation data according to at least one algorithm or routine 208, which is set forth in further detail below. The radiation data is generally stored in a corresponding patient profile 224 within the patient profile database 222. The radiation data may be stored in the patient profile 224 substantially simultaneously with the sensing of the radiation data, or alternatively, may be communicated and stored after the imaging procedure or treatment is completed. Additionally or alternatively, if the radiation data is received without an associate patient name, the radiation data may be stored in a designated location or profile in the management system 200 based on the date information assigned to the radiation data.

In step 266, the radiation data may also be displayed on the user interface assembly 72. The radiation data sensed by the radiation sensors 34 may be communicated to the medical personnel via the display screen 74 of the user interface assembly 72. Additionally or alternatively, the radiation data may be communicated to the medical personnel within the surgical suite by an additional output (for example, an audio output) from the user interface assembly 72. Displaying radiation data allows the medical personnel to actively monitor the radiation dose of the patient during or directly after the imaging procedure or treatment.

According to the method 250, the radiation data sensed by the radiation sensor assembly 30 may be communicated to the management system 200. In this way, the radiation dose received by the patient on the patient support apparatus 10 may be automatically recorded in the patient profile database 222 and displayed on the user interface assembly 72. The radiation sensors 34 may periodically or continuously sense the radiation data from the radiation unit 58. The sensed radiation data may be analyzed by the first controller 160 as the radiation sensors 34 are sensing additional radiation data. Moreover, the radiation data may be communicated to the second controller 202 concurrently with the radiation sensors 34 sensing additional radiation data or after the first controller 160 analyzes the radiation data. As such, the radiation monitoring system 220 may provide "real-time" recording of the radiation dose and/or "real-time" display of the radiation dose received by the patient. This may increase accuracy of the information in the patient profile 224 information, as well as alert medical personnel if the radiation dose received by the patient has exceeded a specified threshold. It is understood that the steps of the method 250 may be performed in any order, simultaneously, and/or omitted without departing from the teachings provided herein.

Figure 11:
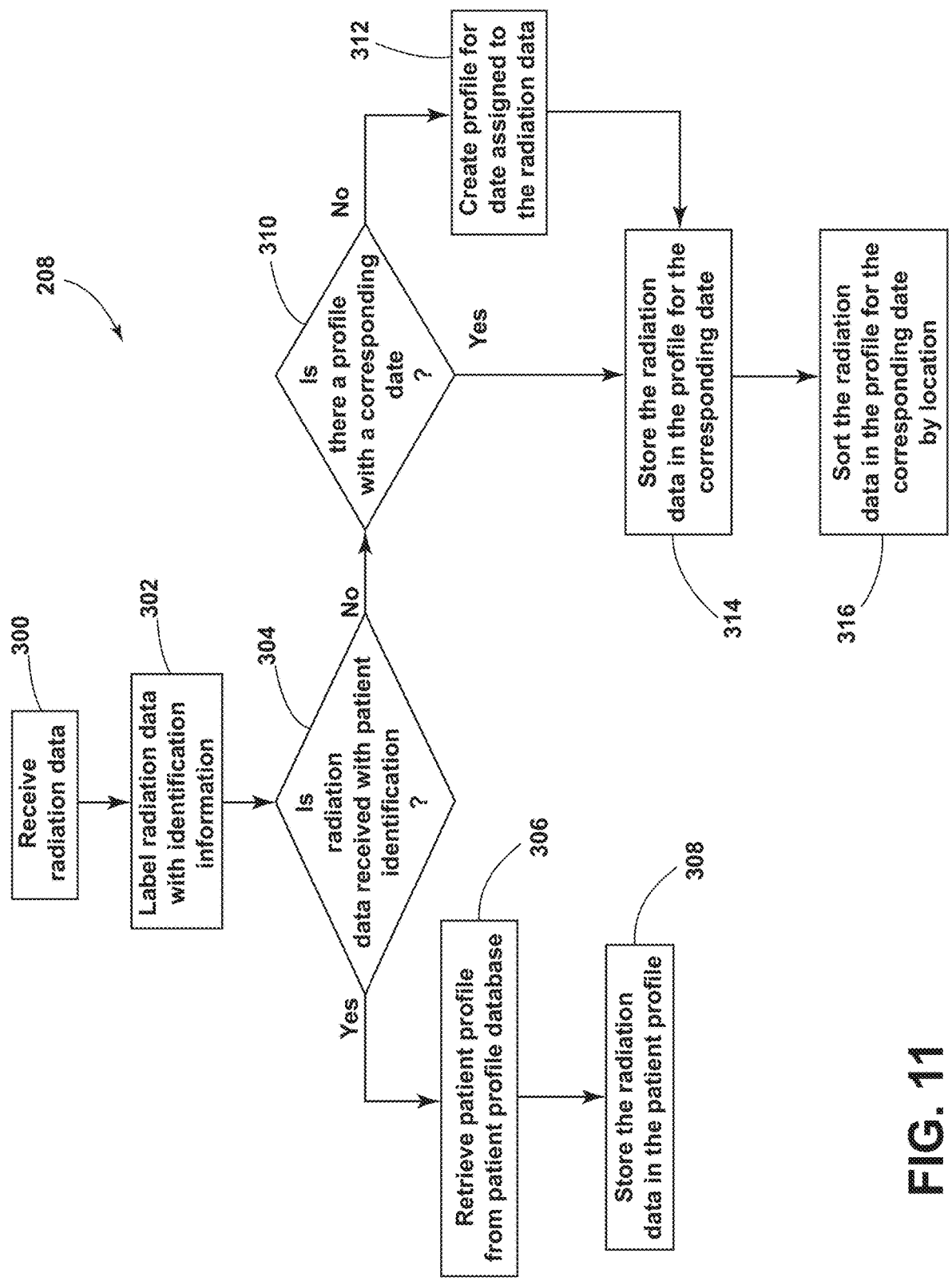
FIG. 11 is a flow diagram of a method of storing and displaying radiation data, according to the present disclosure.

Referring to FIG. 11, as well as FIGS. 1-10, the second controller 202 may include at least one algorithm or routine 208 for storing the radiation data as set forth in step 260 of the method 250. The storing routine 208 begins with step 300 where the second controller 202 receives the radiation data from the first controller 160 via the communication interface 190. In step 302, once the second controller 202 receives the radiation data, the radiation data may be labeled or identified with a date, time, location, or other identifying data. The date and time associated with the radiation data may be identified by the first controller 160 when the radiation data is initially sensed or analyzed or may be input by the medical personnel. The second controller 202 utilizes the date and time information to label the received data. This configuration allows for monitoring when the radiation dose was received and may be advantageous if there is a delay in communicating the information to the second controller 202. Accordingly, the date and time recorded with the radiation data correspond with the date and time that the patient received the radiation dose. The location corresponds with the surgical suite where the radiation unit 58 and the radiation sensor assembly 30 were used. The location information may be advantageous for monitoring certain medical personnel or medical equipment to determine if there may be trends in radiation doses received by patients over time. It is contemplated that the radiation data may be labeled or otherwise identified with additional or alternative information depending on the routine 208.

Once the radiation data is labeled or otherwise identified, at decision step 304 the routine 208 determines whether the radiation data was received with a patient name associated with the radiation data. The medical personnel within the surgical suite may input the patient name or information via the user interface assembly 72. The first controller 160 may associate or link the sensed radiation data received with the patient name or information. The medical personnel may manually input the patient name or information, or alternatively, may scan a barcode associated with the patient name or information.

If the medical personnel inputs the patient name or information, the associated patient profile 224 is retrieved from the patient profile database 222 in step 306. In step 308, the radiation data is stored within the associated patient profile 224. The radiation data may be stored on a continual basis during the imaging procedure. In such examples, the radiation sensor assembly 30 may continually send radiation data to the second controller 202 during the time the radiation unit 58 is in use. Alternatively, the radiation data may be temporarily stored in the first controller 160 until the radiation unit 58 is deactivated. Once the radiation unit 58 is deactivated, the first controller 160 may communicate the radiation data to the second controller 202 for storage. With the patient profile 224 retrieved from the patient profile database 222, the sensed radiation data may be communicated to the second controller 202 and immediately stored with the patient profile 224.

Returning to the decision step 304, if the radiation data was received by the second controller 202 without the patient name or information, in decision step 310 the routine 208 determines if the patient profile database 222 includes a non-patient specific profile with a corresponding date. Stated differently, the routine 208 determines if there is a profile in the patient profile database 222 that is labeled with a date that matches the date of the labeled radiation data. If there is no profile with the corresponding date, a profile is created for the date assigned to the radiation data in step 312. If there is a profile for the corresponding date, the routine 208 may bypass step 312 and proceed to step 314 to store the radiation data in the profile with the corresponding date. In this way, if there is an error, either human-based or system-based, in inputting the name or information of the patient, the radiation data is stored in a profile that corresponds with the date the radiation data was sensed by the radiation sensor assembly 30. Using the location information and the date, the medical personnel may move the radiation data from the non-patient specific folder to the patient profile 224.

In step 316, the routine 208 may sort the radiation data for the corresponding date by location (e.g., surgical suite). This sorting may be completed in the patient profile 224 or the non-patient specific profile for convenience in finding the radiation data at a later time. The routine 208 provides for automatic storage of the radiation data for the patient in the associated patient profile 224, or alternatively, stored by the date or the location of the sensed radiation. The sensed radiation data may be stored for each patient to monitor the radiation dose received during an imaging procedure or treatment. The medical personnel may monitor if the radiation dose received by the patient exceeds a specific threshold. Additionally or alternatively, the radiation doses stored for each patient may collectively be monitored for trends in certain medical personnel or medical equipment or certain health concerns.

Use of the present device may provide for a variety of advantages. For example, the radiation sensor assembly 30 may be adjusted on the support member 14 of the patient support apparatus 10. Further, the adjustment of the radiation sensor assembly 30 may increase the accuracy and efficiency of the radiation sensors 34. Additionally, the radiation sensor assembly 30 may communicate the sensed radiation data to the user interface assembly 72 and the second controller 202 in the management system 200. When the radiation data is sent to the user interface assembly 72, the medical personnel within the surgical suite may be periodically or continuously updated with the radiation dose received by the patient on the patient support apparatus 10. When the radiation data is communicated to the second controller 202, the radiation data may be periodically or continuously stored in the associated patient profile 224. Moreover, the continuous notification to medical personnel and the continuous storage of the radiation data in the patient profile 224 may increase the accuracy and efficiency of the electronic medical records of the patient, while minimizing human-based errors in the recording process. Additionally, the continuous recording and notification may also help prevent adverse health effects as a result of a radiation dose that exceeds a specified threshold. Additional benefits or advantages of using this device may also be realized and/or achieved.

The device disclosed herein is further summarized in the following paragraphs and is further characterized by combinations of any and all of the various aspects described therein.

According to another aspect, a radiation monitoring system includes a patient support apparatus. A radiation sensor assembly is operably coupled to the patient support apparatus. The radiation sensor assembly includes a radiation sensor and a first controller. The radiation sensor senses radiation data corresponding to a radiation dose received by a patient. A management system includes a second controller that stores a patient profile database. The second controller is communicatively coupled with the first controller. The first controller communicates the radiation data to the second controller for storage in the patient profile database to monitor the radiation dose received by the patient.

According to another aspect, a positioning assembly operably coupled to the radiation sensor assembly, wherein the positioning assembly translates the radiation sensor assembly between first and second ends of the patient support apparatus.

According to another aspect, the patient support apparatus defines a cavity for selectively receiving the radiation sensor assembly.

According to another aspect, the second controller of the management system includes patient profiles stored in the patient profile database, and wherein the radiation data is stored within a respective patient profile.

Another to another aspect, a user interface assembly communicatively coupled to the first controller, wherein the first controller communicates the radiation data to the user interface assembly to be displayed by the user interface assembly.

According to another aspect, the radiation sensor includes an adhesive portion and a cover film, and wherein the radiation sensor is removably coupled to the patient support apparatus.

According to another aspect, a position sensor operably coupled to the patient support apparatus, wherein the position sensor senses a position of the radiation sensor.

According to another aspect, a patient support apparatus includes a support member coupled to a base. A radiation sensor assembly is operably coupled to the support member. The radiation sensor assembly includes at least one radiation sensor for sensing radiation data to monitor a radiation dose received by a patient. A positioning assembly is operably coupled to the radiation sensor assembly and the support member. The radiation sensor assembly translates between a first end of the support member and a second end of the support member via the positioning assembly. The radiation sensor assembly remains operably coupled with the support member as the radiation sensor assembly is translated.

According to another aspect, the positioning assembly includes a rail assembly, wherein the radiation sensor assembly is coupled to a rail slide slidably engaged with a rail.

According to another aspect, the positioning assembly includes a belt having a plurality of teeth that engage a gear assembly.

According to another aspect, the positioning assembly includes a motor for automatically adjusting a position of the radiation sensor assembly.

According to another aspect, a position sensor operably coupled to the support member, wherein the position sensor senses a position of the radiation sensor assembly.

According to another aspect, the at least one radiation sensor senses electromagnetic waves having a wavelength in a range of from 0.01 nm to 10 nm.

According to another aspect, the radiation sensor assembly includes a controller for communicating the radiation data to a patient profile.

According to another aspect, the at least one radiation sensor includes an array of radiation sensors arranged between the first end and the second end of the support member.

According to another aspect, a method of monitoring a radiation dose includes: aligning a radiation sensor assembly with a selected area to receive radiation. Radiation is emitted toward a patient support apparatus. Radiation data corresponding to a radiation dose received by a patient is sensed via a radiation sensor assembly. The radiation data is communicated from a first controller of the radiation sensor assembly operably coupled with the patient support apparatus to a second controller of a management system. The radiation data is stored within a selected profile within the management system.

According to another aspect, the radiation sensor assembly is adjusted to a position between an emitter and a detector of a radiation unit.

According to another aspect, identification information is assigned to the radiation data, and the radiation data is stored in the selected profile associated with a patient.

According to another aspect, the radiation data is displayed on a user interface assembly.

According to another aspect, a date is assigned to the radiation data corresponding to when the radiation data was sensed, and the radiation data is stored in the selected profile within the management system corresponding to the date.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

The various illustrative logical blocks, modules, controllers, and circuits described in connection with the embodiments disclosed herein may be implemented or performed with application specific integrated circuits (ASICs), field programmable gate arrays (FPGAs), general purpose processors, digital signal processors (DSPs) or other logic devices, discrete gates or transistor logic, discrete hardware components, or any combination thereof designed to perform the functions described herein. A general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A patient support apparatus, comprising:
   a support member;
   a base operably coupled to the support member;
   a pedestal extending between the support member and the base;
   a radiation sensor assembly operably coupled to the support member, wherein the radiation sensor assembly includes:
      a radiation sensor configured to be positioned between an emitter and a detector of an X-ray machine; and
      a controller operably coupled to the radiation sensor, wherein the controller is configured to correlate the radiation sensor with a location on the support member.

2. The patient support apparatus of claim 1, further comprising:
   a positioning assembly configured to translate the radiation sensor between opposing ends of the support member.

3. The patient support apparatus of claim 2, wherein the positioning assembly is configured to adjust the radiation sensor to a focus area of a radiation unit.

4. The patient support apparatus of claim 1, wherein the controller is configured to determine an amount of hard X-rays and soft X-rays sensed by the radiation sensor.

5. The patient support apparatus of claim 1, wherein the support member defines multiple cavities arranged along a length thereof, and wherein the radiation sensor is configured to be selectively positioned in the multiple cavities to align the radiation sensor with a focus area of a radiation unit.

6. The patient support apparatus of claim 1, wherein the radiation sensor is adhered to the support member.

7. The patient support apparatus of claim 1, further comprising:
   an indicator operably coupled to the radiation sensor assembly, wherein the indicator is configured to provide notification that the radiation sensor is at a selected location.

8. A patient support apparatus, comprising:
   a support member coupled to a base;
   a radiation sensor assembly operably coupled to the support member, wherein the radiation sensor assembly includes at least one radiation sensor for sensing radiation data to monitor a radiation dose received by a patient; and
   a positioning assembly operably coupled to the radiation sensor assembly and the support member, wherein the radiation sensor assembly translates between a first end of the support member and a second end of the support member via the positioning assembly, and wherein the radiation sensor assembly remains operably coupled with the support member as the radiation sensor assembly is translated.

9. The patient support apparatus of claim 8, wherein the positioning assembly includes a rail assembly, and wherein the radiation sensor assembly is coupled to a rail slide slidably engaged with a rail.

10. The patient support apparatus of claim 8, wherein the positioning assembly includes a belt having a plurality of teeth that engage a gear assembly.

11. The patient support apparatus of claim 8, wherein the positioning assembly includes a motor for automatically adjusting a position of the radiation sensor assembly.

12. The patient support apparatus of claim 8, further comprising:
a position sensor operably coupled to the support member, wherein the position sensor senses a position of the radiation sensor assembly.

13. The patient support apparatus of claim 8, wherein the at least one radiation sensor senses electromagnetic waves having a wavelength in a range of from 0.01 nm to 10 nm.

14. The patient support apparatus of claim 8, wherein the radiation sensor assembly includes a controller for communicating the radiation data to a patient profile.

15. The patient support apparatus of claim 8, wherein the at least one radiation sensor includes an array of radiation sensors arranged between the first end and the second end of the support member.

16. A patient support apparatus, comprising:
a base;
a support member operably coupled to the base; and
a radiation sensor assembly operably coupled to the support member, wherein the radiation sensor assembly includes:
an array of radiation sensors arranged along the support member; and
a controller operably coupled to the array of radiation sensors, wherein the controller is configured to determine an amount of radiation sensed by each of the array of radiation sensors.

17. The patient support apparatus of claim 16, wherein each radiation sensor of the array of radiation sensors is configured to be independently activated based on a location of a radiation unit.

18. The patient support apparatus of claim 16, wherein the array of radiation sensors are disposed along a central longitudinal axis of the support member.

19. The patient support apparatus of claim 16, wherein the support member includes multiple segments, and wherein the array of radiation sensors is arranged in groupings, each grouping corresponding to one of the multiple segments of the support member.

20. The patient support apparatus of claim 19, wherein a position of each radiation sensor is configured to be adjusted within a respective one of the multiple segments.

* * * * *